United States Patent
Hoffman et al.

(10) Patent No.: US 7,773,793 B2
(45) Date of Patent: Aug. 10, 2010

(54) COMPUTERIZED METHOD AND SYSTEM FOR ASSOCIATING A PORTION OF A DIAGNOSTIC IMAGE WITH AN ELECTRONIC RECORD

(75) Inventors: Mark A. Hoffman, Lee's Summit, MO (US); Louis M. Humphrey, Durham, NC (US); David M. Duello, Kansas City, MO (US)

(73) Assignee: Cerner Innovation, Inc., Overland Park, KS (US)

( * ) Notice: Subject to any disclaimer, the term of this patent is extended or adjusted under 35 U.S.C. 154(b) by 0 days.

(21) Appl. No.: 12/048,816

(22) Filed: Mar. 14, 2008

(65) Prior Publication Data

US 2008/0166031 A1   Jul. 10, 2008

Related U.S. Application Data

(62) Division of application No. 10/873,660, filed on Jun. 22, 2004.

(51) Int. Cl.
*G06K 9/00* (2006.01)

(52) U.S. Cl. .................. 382/129; 382/128; 600/407

(58) Field of Classification Search ................ 382/128, 382/131, 129; 705/3; 600/407
See application file for complete search history.

(56) References Cited

U.S. PATENT DOCUMENTS

| | | | |
|---|---|---|---|
| 4,654,872 A | 3/1987 | Hisano et al. | |
| 4,825,388 A * | 4/1989 | Dailey et al. | 345/595 |
| 4,858,157 A | 8/1989 | Murai et al. | |
| 4,938,591 A * | 7/1990 | Anderson et al. | 356/73 |
| 5,262,856 A | 11/1993 | Lippman et al. | |
| 5,274,453 A | 12/1993 | Maeda | |
| 5,530,420 A | 6/1996 | Tsuchiya et al. | |
| 5,684,887 A | 11/1997 | Lee et al. | |
| 5,904,822 A * | 5/1999 | Casavant | 204/461 |
| 6,031,568 A | 2/2000 | Wakitani | |
| 6,059,404 A | 5/2000 | Jaeger et al. | |
| 6,285,781 B1 * | 9/2001 | Yamazaki | 382/132 |
| 6,640,000 B1 * | 10/2003 | Fey et al. | 382/128 |
| 6,675,166 B2 * | 1/2004 | Bova | 707/10 |

(Continued)

OTHER PUBLICATIONS

Office Action, mailed Oct. 14, 2009 for U.S. Appl. No. 10/873,660.

(Continued)

*Primary Examiner*—Daniel G Mariam
*Assistant Examiner*—Aklilu k Woldemariam
(74) *Attorney, Agent, or Firm*—Shook, Hardy & Bacon

(57) ABSTRACT

A computerized method for associating one or more portions of a diagnostic image with one or more electronic records is provided. The method includes receiving a diagnostic image having data particular to at least two persons and associating a first portion of the diagnostic image with an electronic record. The method may further include storing the first portion of the diagnostic image with the electronic record and/or associating and storing a common portion of the diagnostic image with the electronic record, the common portion consisting of data common to each person whose data is shown on the image. In one embodiment, the method may further include modifying the received diagnostic image and associating and storing the modified image with an electronic record. A computer system for associating at least a portion of a diagnostic image with an electronic record is also provided.

22 Claims, 6 Drawing Sheets

U.S. PATENT DOCUMENTS

| | | | |
|---|---|---|---|
| 6,690,451 | B1 | 2/2004 | Schubert |
| 6,980,674 | B2 * | 12/2005 | Anderson et al. ............ 382/128 |
| 7,000,186 | B1 | 2/2006 | Gropper et al. |
| 7,050,909 | B2 | 5/2006 | Nichols et al. |
| 7,242,817 | B2 | 7/2007 | Takeda et al. |
| 7,499,578 | B2 | 3/2009 | Reeves et al. |
| 2002/0001401 | A1 * | 1/2002 | Bocionek ................... 382/128 |
| 2002/0001406 | A1 | 1/2002 | Kochi et al. |
| 2002/0019751 | A1 * | 2/2002 | Rothschild et al. ............. 705/3 |
| 2002/0114501 | A1 * | 8/2002 | Taylor, Jr. ................... 382/128 |
| 2002/0164060 | A1 | 11/2002 | Paik et al. |
| 2002/0180870 | A1 | 12/2002 | Chen |
| 2002/0181745 | A1 | 12/2002 | Hu |
| 2003/0005464 | A1 | 1/2003 | Gropper et al. |
| 2003/0048933 | A1 * | 3/2003 | Brown et al. ................ 382/128 |
| 2003/0177446 | A1 | 9/2003 | Gropper et al. |
| 2004/0086163 | A1 * | 5/2004 | Moriyama et al. .......... 382/131 |
| 2004/0105493 | A1 | 6/2004 | Kondo et al. |
| 2004/0125984 | A1 | 7/2004 | Ito et al. |
| 2004/0146190 | A1 * | 7/2004 | Kasai ........................ 382/128 |
| 2005/0283062 | A1 * | 12/2005 | Hoffman et al. ............ 600/407 |
| 2009/0110251 | A1 | 4/2009 | Hoffman |

OTHER PUBLICATIONS

Office Action, mailed Nov. 28, 2008 for U.S. Appl. No. 10/873,660.
Office Action, mailed Apr. 11, 2008 for U.S. Appl. No. 10/873,660.
Office Action, mailed Jan. 8, 2008 for U.S. Appl. No. 10/873,660.
Office Action mailed Mar. 2, 2010 for U.S. Appl. No. 12/350,430.
Nonlinear Dynamics Ltd., TotalLab Applications, Image analysis software for ID electrophoresis gels, arrays, blots and colonies, www.nonlinear.com website, published Sep. 21, 2004.

* cited by examiner

COMPUTERIZED METHOD AND SYSTEM FOR ASSOCIATING A PORTION OF A DIAGNOSTIC IMAGE WITH AN ELECTRONIC RECORD

CROSS-REFERENCE TO RELATED APPLICATIONS

This application is a Divisional Application that claims the benefit of U.S. patent application Ser. No. 10/873,660 filed Jun. 22, 2004, entitled COMPUTERIZED METHOD AND SYSTEM FOR ASSOCIATING A PORTION OF A DIAGNOSTIC IMAGE WITH AN ELECTRONIC RECORD, herein incorporated by reference.

STATEMENT REGARDING FEDERALLY SPONSORED RESEARCH OR DEVELOPMENT

Not applicable.

TECHNICAL FIELD

The present invention relates generally to the field of computer software. More particularly, the present invention relates to a computerized method and system for associating one or more portions of a diagnostic image, the image including data particular to at least two persons, with one or more electronic records, for instance, electronic medical records maintained in a clinical information system.

BACKGROUND OF THE INVENTION

A common process in the molecular diagnostic laboratory is the generation of gel results. Gels are typically used to analyze deoxyribonucleic acid (DNA), ribonucleic acid (RNA) and protein results, although they may also be used to analyze other biological molecules such as lipids, oligosaccharides, and the like. A gel is a viscous substance, typically agarose or acrylamide, having a plurality of recessed portions, commonly known as wells, into which various samples may be loaded for analysis. Subsequent to loading, an electric current may be applied to the gel, pulling charged molecules of the samples through the gel. When the current has ceased, the position of the molecules relative to one another may provide useful information about various attributes, e.g., charge and/or size, of the molecule or molecules being examined, presence or absence of mutations and gene rearrangements. The information derived from the gel results may then be used to make an array of diagnostic decisions.

After a gel has been run (i.e., after the current has ceased), a substantially linear region results from each loaded well. The linear regions are commonly referred to as lanes. Due to, for instance, efficiency concerns, a plurality of samples are generally run on a single gel and, thus, a plurality of lanes results when the gel is run. In a clinical setting, this commonly results in a single gel including lanes having results from more than one individual. Additionally, one or more reference lanes are typically run on each gel. The reference lanes may include, for example, molecular weight markers and/or positive and negative controls.

Long-term management of a gel typically involves capturing and storing an image (e.g., a photographic image) of the gel rather than maintaining the gel itself. Traditional gel image management, designed primarily to meet the needs of the research community, focuses on storing an image of the entire gel. However, in a clinical setting, storing an image of an entire gel, which often includes data from a plurality of individuals, presents a significant privacy concern. For example, suppose five individuals visit an AIDS clinic on the same day to determine whether or not they are HIV+. Each of the five individuals is seated in the waiting room at the same time. Samples from each individual are loaded into a single gel and the gel is run resulting in one lane for each individual. Now suppose that although a particular one of those five individuals receives the news that she is not HIV+, she wishes to view the test results herself. Since an image of that individual's test results is a complete gel image including the lanes from the other four individuals in the waiting room, she retrieves not only her own results but those of the other four individuals as well. If the results indicate that one of the individuals tested is HIV+, even though that person's identity is not specifically set forth on the gel image, the individual in possession of the gel image would easily be able to deduce that one of the other four individuals in the waiting room is HIV+. Such disclosure of another individual's test results, though inadvertent, is clearly undesirable.

Additionally, in the clinical setting, current association of a gel image with an individual's medical record is achieved by paper-based means. That is, a photocopy of the entire gel image is physically placed in the paper record of each individual having results shown on the image. However, modern clinical information systems manage the medical records of many individuals in electronic form. Since the gel image is a paper copy while much of the remainder of the medical record is electronic, the only means by which the gel image may be associated with the electronic record is via a reference placed in the electronic record indicating that the person inquiring about the test results must access the paper record. This is clearly an inefficient and inconvenient approach.

In view of the above, the inventors hereof have recognized that a method of integrating gel image results into an individual's medical record in a manner that conveys the appropriate clinical information to the healthcare provider while protecting the privacy of the other individuals whose results are represented on the gel image would be desirable. Additionally, a means for electronic association of one or more portions of a diagnostic image with one or more individual's electronic records would be advantageous.

SUMMARY OF THE INVENTION

The present invention provides a method in a computing environment for associating one or more portions of a diagnostic image with one or more electronic records, for instance, electronic medical records maintained in a clinical information system. The method may include receiving a diagnostic image having data particular to at least two persons and associating a first portion of the diagnostic image with an electronic record. The method may further include storing the first portion of the diagnostic image with the electronic record. Additionally, if desired, the method may include associating and storing a common portion of the diagnostic image with the electronic record, the common portion consisting of data common to each person whose data is shown on the image.

The present invention further provides a method in a computing environment for associating one or more portions of a diagnostic image with one or more electronic records, e.g., electronic medical records. The method may include receiving a diagnostic image having data particular to at least two persons, modifying the diagnostic image to create a modified image, and associating the modified image with an electronic record. The method may further include storing the modified image with the electronic record.

A computer-readable medium having computer-executable instructions for performing the methods disclosed herein are also provided.

Additionally, the present invention provides a computer system for associating at least a portion of a diagnostic image with an electronic record. The computer system may include an receiving module for receiving a diagnostic image having data particular to at least two persons and an association module for associating a portion of the diagnostic image with the electronic record. If desired, the computer system may further include a modification module for modifying the diagnostic image to create a modified image and a storage module for storing the portion of the diagnostic image and/or the modified image with the electronic record.

BRIEF DESCRIPTION OF THE SEVERAL VIEWS OF THE DRAWINGS

The present invention is described in detail below with reference to the attached drawing figures, wherein.

DETAILED DESCRIPTION OF THE INVENTION

Figure 1:
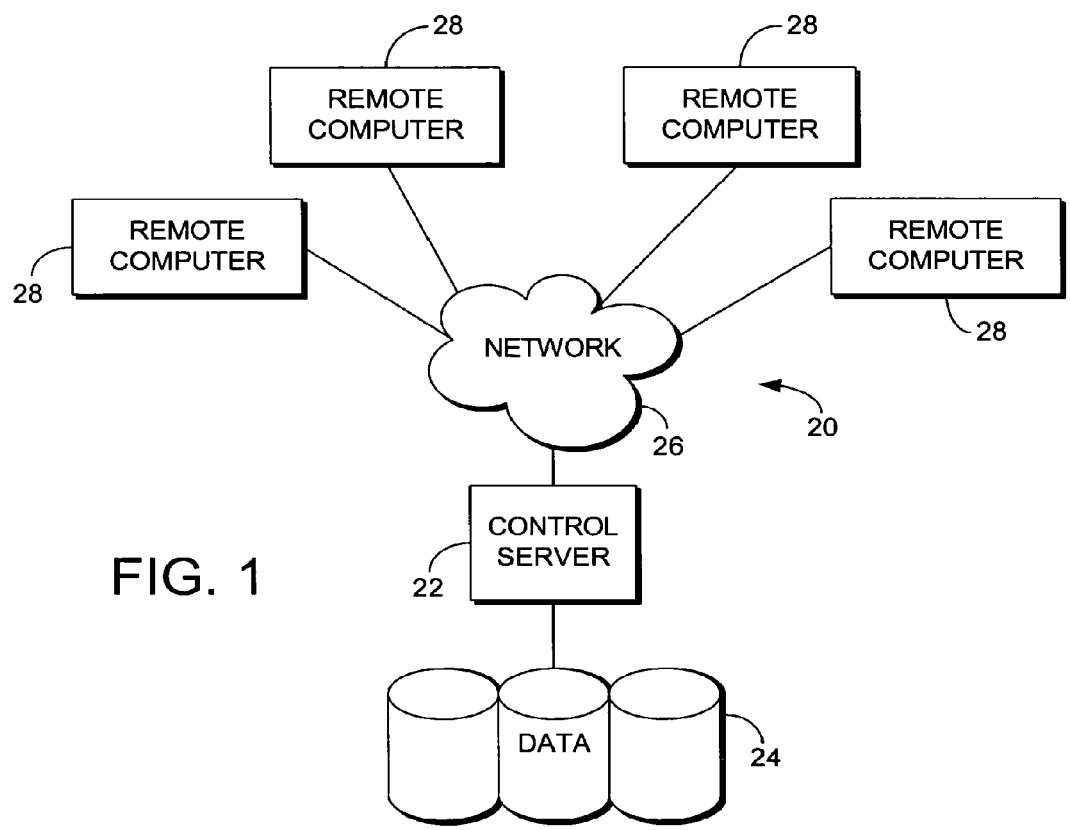
FIG. 1 is a block diagram of a computing system environment suitable for use in implementing the present invention.

Referring to the drawings in general, and initially to FIG. 1 in particular, an exemplary computing system environment, for instance, a medical information computing system environment, on which the present invention may be implemented is illustrated and designated generally as reference numeral 20. It will be understood and appreciated by those of ordinary skill in the art that the illustrated medical information computing system environment 20 is merely an example of one suitable computing environment and is not intended to suggest any limitation as to the scope of use or functionality of the invention. Neither should the medical information computing system environment 20 be interpreted as having any dependency or requirement relating to any single component or combination of components illustrated therein.

The present invention may be operational with numerous other general purpose or special purpose computing system environments or configurations. Examples of well-known computing systems, environments, and/or configurations that may be suitable for use with the present invention include, by way of example only, personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention may be described in the general context of computer-executable instructions, such as program modules, being executed by a computer. Generally, program modules include, but are not limited to, routines, programs, objects, components, and data structures that perform particular tasks or implement particular abstract data types. The present invention may also be practiced in distributed computing environments where tasks are performed by remote processing devices that are linked through a communications network. In a distributed computing environment, program modules may be located in local and/or remote computer storage media including, by way of example only, memory storage devices.

With continued reference to FIG. 1, the exemplary medical information computing system environment 20 includes a general purpose computing device in the form of a control server 22. Components of the control server 22 may include, without limitation, a processing unit, internal system memory, and a suitable system bus for coupling various system components, including database cluster 24, with the control server 22. The system bus may be any of several types of bus structures, including a memory bus or memory controller, a peripheral bus, and a local bus, using any of a variety of bus architectures. By way of example, and not limitation, such architectures include Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 22 typically includes therein, or has access to, a variety of computer readable media, for instance, database cluster 24. Computer readable media can be any available media that may be accessed by control server 22, and includes volatile and nonvolatile media, as well as removable and nonremovable media. By way of example, and not limitation, computer readable media may include computer storage media and communication media. Computer storage media may include, without limitation, volatile and nonvolatile media, as well as removable and nonremovable media implemented in any method or technology for storage of information, such as computer readable instructions, data structures, program modules, or other data. In this regard, computer storage media may include, but is not limited to, RAM, ROM, EEPROM, flash memory or other memory technology, CD-ROM, digital versatile disks (DVDs), or other optical disk storage, magnetic cassettes, magnetic tape, magnetic disk storage, or other magnetic storage devices, or any other medium which can be used to store the desired information and which may be accessed by control server 22. Communication media typically embodies computer readable instructions, data structures, program modules, or other data in a modulated data signal, such as a carrier wave or other transport mechanism, and may include any information delivery media. As used herein, the term "modulated data signals" refers to a signal that has one or more of its characteristics set or changed in such a manner as to encode information in the signal. By way of example, and not limitation, communication media includes wired media such as a wired network or direct-wired connection, and wireless media such as acoustic, RF, infrared, and other wireless media. Combinations of any of the above also may be included within the scope of computer readable media.

The computer storage media discussed above and illustrated in FIG. 1, including database cluster 24, provide storage of computer readable instructions, data structures, program modules, and other data for control server 22.

The control server 22 may operate in a computer network 26 using logical connections to one or more remote computers 28. Remote computers 28 may be located at a variety of locations in a medical environment, for example, but not limited to, clinical laboratories, hospitals and other inpatient settings, ambulatory settings, medical billing and financial offices, hospital administration settings, home health care environments, and clinicians' offices. Clinicians may include, but are not limited to, a treating physician or physicians, specialists such as surgeons, radiologists and cardiologists, emergency medical technicians, physicians' assistants, nurse practitioners, nurses, nurses' aides, pharmacists, dieticians, microbiologists, and the like. Remote computers 28 may also be physically located in non-traditional medical care environments so that the entire health care community may be capable of integration on the network. Remote computers 28 may be personal computers, servers, routers, network PCs, peer devices, other common network nodes, or the like, and may include some or all of the elements described above in relation to the control server 22.

Exemplary computer networks 26 may include, without limitation, local area networks (LANs) and/or wide area networks (WANs). Such networking environments are commonplace in offices, enterprise-wide computer networks, intranets, and the Internet. When utilized in a WAN networking environment, the control server 22 may include a modem or other means for establishing communications over the WAN, such as the Internet. In a networked environment, program modules or portions thereof may be stored in the control server 22, in the database cluster 24, or on any of the remote computers 28. For example, and not by way of limitation, various application programs may reside on the memory associated with any one or all of the remote computers 28. It will be appreciated by those of ordinary skill in the art that the network connections shown are exemplary and other means of establishing a communications link between the computers (e.g., control server 22 and remote computers 28) may be utilized.

In operation, a user may enter commands and information into the control server 22 or convey the commands and information to the control server 22 via one or more of the remote computers 28 through input devices, such as a keyboard, a pointing device (commonly referred to as a mouse), a trackball, or a touch pad. Other input devices may include, without limitation, microphones, satellite dishes, scanners, or the like. The control server 22 and/or remote computers 28 may further include a display device, for instance, a monitor. Additionally, the control server 22 and/or remote computers 28 may include other peripheral output devices, such as speakers and a printer.

Although many other internal components of the control server 22 and the remote computers 28 are not shown, those of ordinary skill in the art will appreciate that such components and their interconnection are well known. Accordingly, additional details concerning the internal construction of the control server 22 and the remote computers 28 are not further disclosed herein.

Figure 2A:
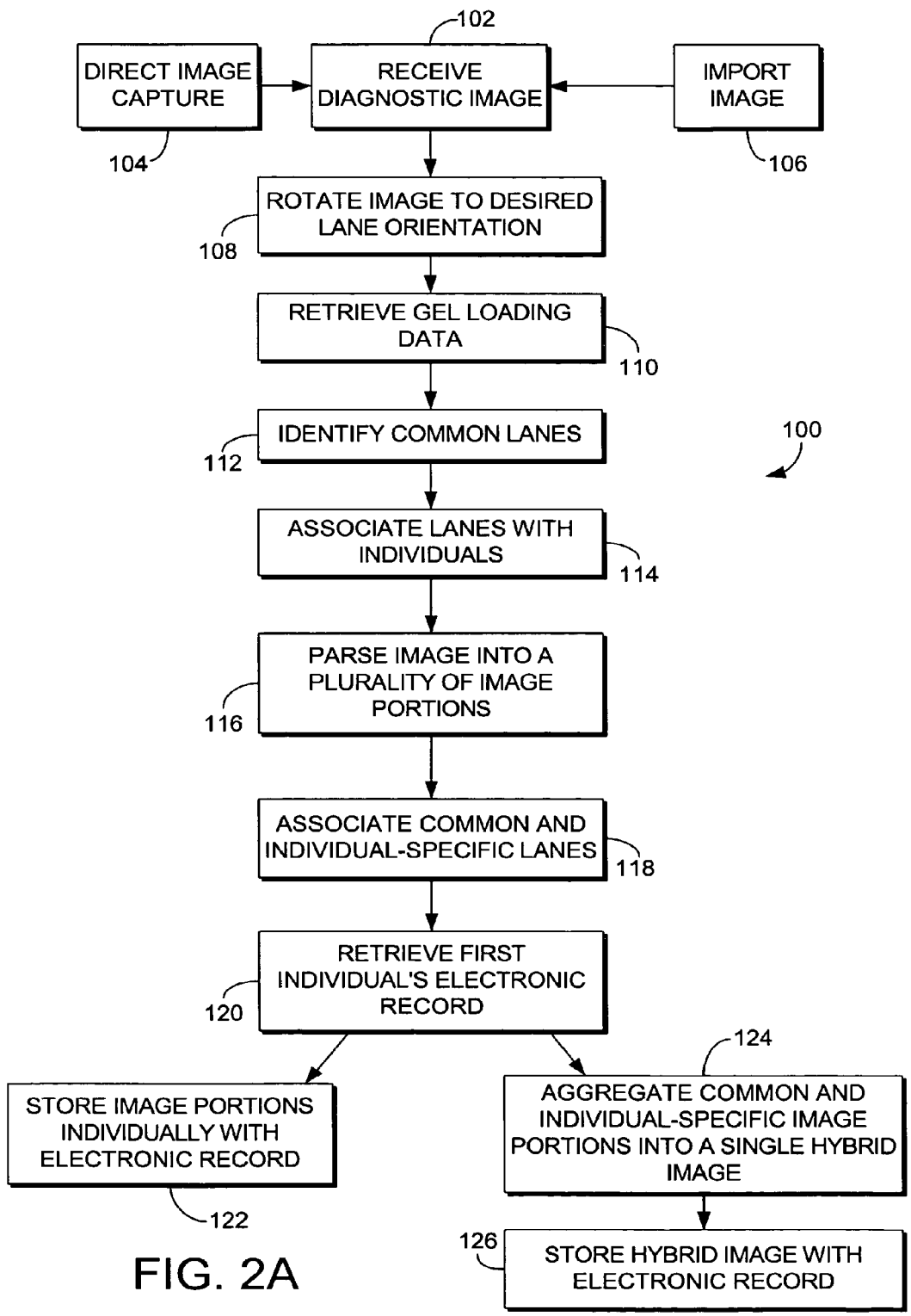
FIG. 2A is a flow chart representative of a computer program for associating at least a portion of a parsed diagnostic image with an electronic record in accordance with an embodiment of the present invention.

With reference to FIG. 2A, a method 100, which may be implemented on the above-described exemplary computing system environment 20 (FIG. 1), for dynamically cropping or parsing a diagnostic image and associating one or more portions of the parsed image with an electronic record which is correlated with an individual whose data is shown on the image is provided. By way of example only, the method 100 of FIG. 2A may be utilized to associate one or more discrete portions of a diagnostic gel image with one or more individuals' electronic medical records, the discrete portions being selected based upon the data contained therein. That is, common or reference data and/or data particular to the individual in question may be associated with that individual's electronic medical record without associating data contained in other portions of the complete image. (The terms "individual", "person", and "patient" are used interchangeably herein and are not meant to limit the nature of the referenced individual in any way. Rather, the methods and systems described herein are equally applicable in, for instance, a veterinary setting. Further, use herein of the term "patient" is not meant to imply any particular relationship between the individual in question and those administering or interpreting the diagnostic tests being implemented.)

Initially, at block 102, the system receives a complete diagnostic image, e.g., a diagnostic gel image, having data shown thereon which is particular to at least two persons. If desired, the complete diagnostic image may further include common or reference data thereon, which data is common to all persons having data shown on the gel. Examples of common data may include, by way of example only, molecular weight markers, positive controls, and/or negative controls.

Figure 3A:
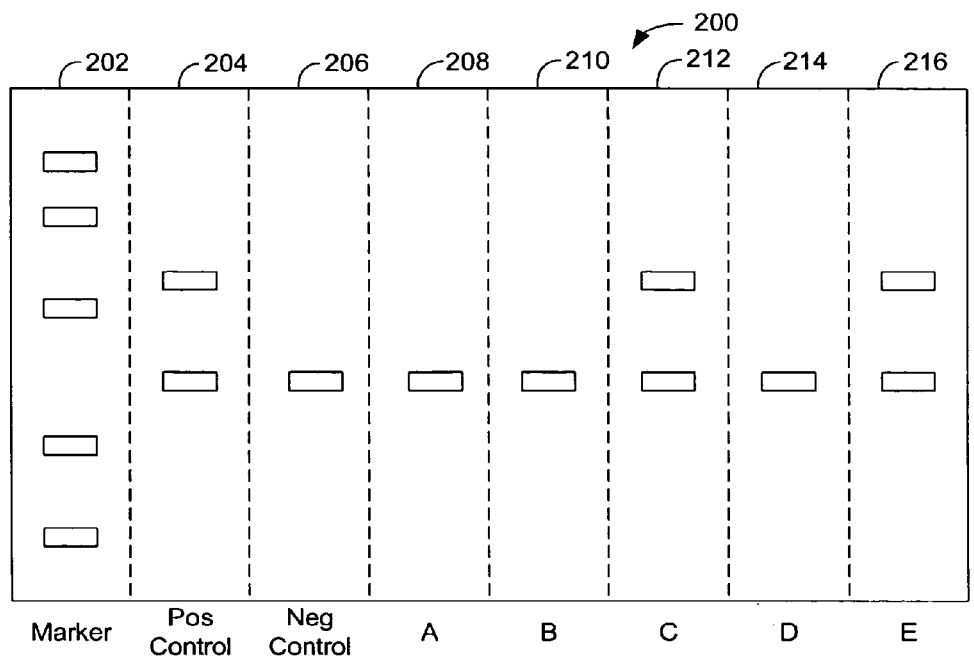
FIG. 3A is a schematic diagram illustrating an exemplary complete gel image having eight lanes.

Referring to FIG. 3A, an exemplary complete diagnostic gel image is illustrated and designated generally as reference numeral 200. The diagnostic gel image 200 includes eight lanes, three of which are common lanes 202, 204, 206 and five of which (labeled 208, 210, 212, 214, and 216) are particular to various individuals. Common lane 202 illustrates a number of molecular weight markers, common lane 204 illustrates a positive control, and common lane 206 illustrates a negative control. Individual-specific lane 208 illustrates data particular to Person A, individual-specific lane 210 illustrates data particular to Person B, individual-specific lane 212 illustrates data particular to Person C, individual-specific lane 214 illustrates data particular to Person D, and individual-specific lane 216 illustrates data particular to Person E.

Referring back to FIG. 2A, the diagnostic image, e.g., diagnostic gel image 200, may be received through direct capture (as indicated at block 104), for instance using a charge-coupled device (CCD) camera or the like, or the diagnostic image maybe imported from another application, for instance, in jpeg, gif, tif, or other file format known to those of ordinary skill in the art. Such image import is indicated at block 106.

Figure 3B:
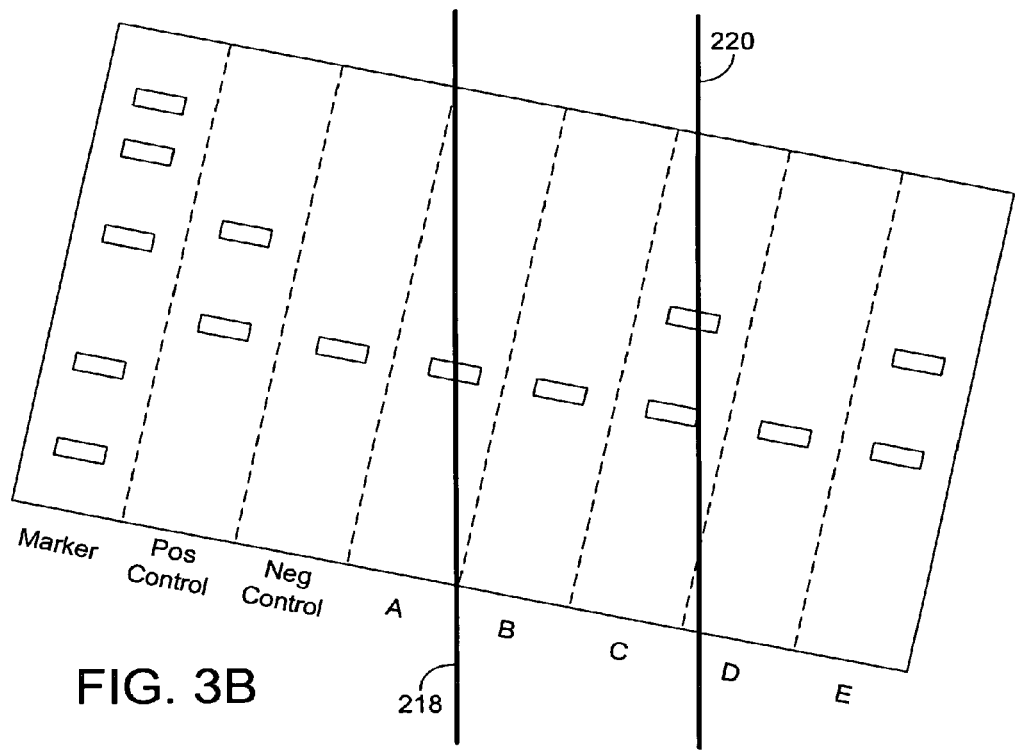
FIG. 3B is a schematic diagram illustrating the exemplary complete gel image of FIG. 3A in a skewed orientation relative to two reference lines setting forth the desired plane for lane orientation.

On occasion, an received diagnostic image may not have the desired image orientation upon import or capture. For instance, the diagnostic image may have a skewed orientation relative to one or more reference indicators 218, 220, as illustrated in FIG. 3B. In such instances, it may be desirable to realign the diagnostic image prior to management thereof to ensure that the correct and appropriate data is derived upon manipulation. This is shown at block 108 of the method of FIG. 2A. Tools, whether manually performed by a user or automatically implemented by the system, for aligning an image based upon a variety of arbitrary rotation criteria are known to those of ordinary skill in the art and, accordingly, are not further described herein. If the received image is in the desired orientation upon capture or import, block 108 may be skipped.

Additionally, it may be necessary or desirable to convert an received image into a digital format recognized by the computing system environment prior to management thereof (not shown). Again, tools for performing such conversion are known to those of ordinary skill in the art and, accordingly, are not further described herein.

Subsequently, as shown at block 110, the system retrieves the gel loading data, i.e., the record indicating which samples were loaded into which wells and, accordingly, which lanes are indicative of common data and which lanes are particular to which individuals. The gel loading data may be maintained as a paper record and input into the system by a user or maintained in an electronic format. In a currently preferred embodiment, a list of persons having data shown on the gel image may be retrieved by the system from a batch list associated with the gel loading process. In a clinical setting, such a batch list may be generated by a clinical laboratory system such as the Cerner Millennium® PathNet® Laboratory Information System available from Cerner Corporation of Kansas City, Mo.

Next, as shown at block 112, the lanes having common data, i.e., data which is common to all persons having data represented on the gel, are identified. Common data identification may be performed manually by a user or electronically by the system depending, in part, in which format the gel loading data is retrieved. As previously stated, examples of common or reference data may include molecular weight markers, positive controls, and/or negative controls. In the diagnostic gel image 200 shown in FIG. 3A, the lanes labeled 202, 204, and 206 are common lanes.

Referring back to FIG. 2A, the lanes which are not identified as common lanes are subsequently associated with the particular individual whose data is shown thereon. This is indicated at block 114. As previously discussed, in the diagnostic gel image 200 of FIG. 3A, the lane labeled 208 is associated with Person A, the lane labeled 210 is associated with Person B, the lane labeled 212 is associated with Person C, the lane labeled 214 is associated with Person D, and the lane labeled 216 is associated with Person E. Again, such association may be performed manually by a user or electronically by the system.

Figure 4:
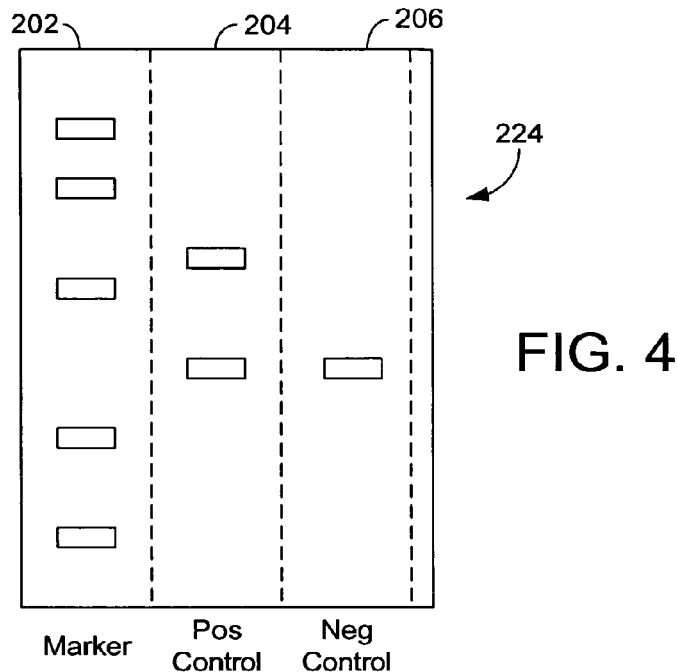
FIG. 4 is a schematic diagram illustrating an exemplary common gel portion derived from the complete gel image shown in FIG. 3A.

Subsequently, as shown at block 116 of FIG. 2A, the diagnostic gel image is parsed into a plurality of image portions. An "image portion", as the term is used herein, is any portion of the diagnostic image which includes less than the entire or complete diagnostic image. Typically, such dynamic parsing is performed by a user viewing the complete diagnostic image on a user interface, such as a monitor. However, electronic parsing performed by the system, preferably with user verification, is also contemplated to be within the scope of the present invention. In one embodiment, the complete diagnostic image may be parsed on a lane-by-lane basis. According to this embodiment, the diagnostic gel image 200 of FIG. 3A would be parsed into eight discrete image portions, one for each lane shown on the image. If desired, however, more than one lane may be included in a single image portion. For instance, in diagnostic gel image 200, there are three common lanes 202, 204, 206 which are positioned next to one another on the image. As such, a single image portion may be easily parsed from the complete image 200 which includes all three common lanes 202, 204, 206. Such single parsed image containing all three common lanes, and designated generally by reference numeral 224, is shown in FIG. 4.

Figure 5:
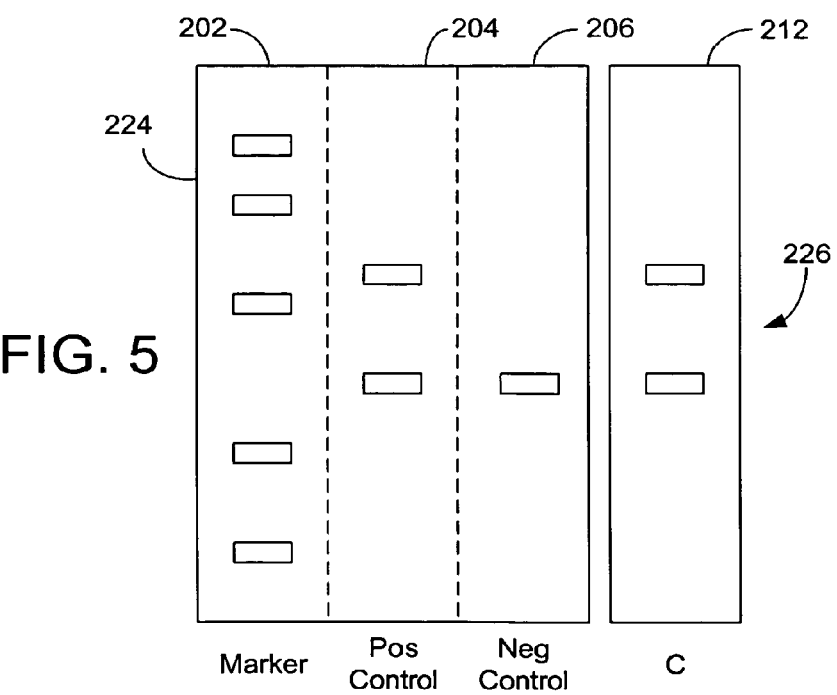
FIG. 5 is a schematic diagram illustrating association of the common gel portion of FIG. 4 with a particular lane of the exemplary complete gel image of FIG. 3A.

After the diagnostic image is parsed into a plurality of image portions, all common image portions, if any, may be associated with the image portion or portions which are particular to a first individual whose data is shown on the image. This association, which may be performed manually by a user or automatically by the system, is indicated at block 118 of FIG. 2A. This association may result in placing the common lane(s) and the associated individual-specific lane(s) in their original position relative to the original complete diagnostic image or collapsing (i.e., pushing) them together where appropriate. For instance, in the schematic diagram of FIG. 5, the common image portion 224 is associated, in side-by-side collapsed orientation, with a single lane parsed image portion showing only the lane labeled 212, which lane is associated with Person C (see, FIG. 3A). The associated image portions are collectively designated by reference numeral 226 in FIG. 5. In this embodiment, the individual-specific lanes and the common lanes maintain the proper orientation with respect to one another. If the diagnostic image does not contain any common or reference data, block 118 may be skipped.

Next, as shown at block 120 of FIG. 2A, the system retrieves an electronic record, e.g., an electronic medical record, correlated with the first individual, i.e., the individual whose data was associated with the common portions at block 118. For example, in the example illustrated in FIG. 5, an electronic record correlated with Person C may be retrieved. If the diagnostic image does not contain any common data and, accordingly, block 118 is skipped, the system may retrieve an electronic record correlated with a first individual whose data is shown on the image at block 120.

Subsequently, the system may individually store the associated image portions with the first individual's electronic record. This is indicated at block 122 of FIG. 2A. In this embodiment, an identifier associated with the complete gel image, e.g., a gel ID number, may be associated with each stored image portion. Thus, upon retrieval of the first individual's electronic record, each image portion may be separately retrieved and viewed, for instance, in side-by-side orientation or overlaid, one upon the other.

In another embodiment, the system may aggregate the common image portion(s) and image portion(s) which are particular to the first individual into a single hybrid image. This is shown at block 124 of FIG. 2A. Subsequently, as shown at block 126, an identifier associated with the complete gel image may be associated with the hybrid image and the system may store the hybrid image with the first individual's electronic record. As such, upon retrieval of the first individual's electronic record, the single hybrid image may be retrieved and all relevant data derived from the diagnostic image viewed as one image. In the example illustrated in FIG. 5, reference numeral 226 indicates a single hybrid image that may be associated and stored with an electronic record correlated with Person C.

Blocks 118, 120, 122, 124, and 126 may be repeated for each individual whose data is shown on the complete diagnostic image, e.g., diagnostic gel image 200 (FIG. 3A). Once all relevant data has been associated with and stored with the electronic record(s) of the person(s) whose data is shown on the complete diagnostic image, the complete image may be destroyed or stored in a location not correlated with any one person's electronic record. In this way, the privacy of all individuals whose data is shown on the image may be maintained.

It will be understood and appreciated by those of ordinary skill in the art that blocks of method 100 may take place in an order other than the exemplary sequence illustrated in FIG. 2A.

In operation, by way of example only, suppose five individuals, designated as Persons A-E visit an AIDS clinic on the same day to determine whether or not they are HIV+. Molecular samples from each of the individuals may be loaded into a single agarose gel. Additionally, three common lanes including molecular weight markers, a positive control, and a negative control also may be loaded into the gel. Viewing the gel from above with each of the wells aligned near the top edge thereof and numbered from 1-8 in a left to right orientation, the molecular weight markers may be loaded into well 1, the positive control may be loaded into well 2, the negative control may be loaded into well 3, the sample from Person A may be loaded into well 4, the sample from Person B may be loaded into well 5, the sample from Person C may be loaded into well 6, the sample from Person D may be loaded into well 7, and the sample from Person E may be loaded into well 8. Subsequently, an electric current may be applied to the gel pulling charged molecules of the samples through the gel. Once the current has ceased, eight lanes may appear on the gel. Referring to FIG. 3A, the lane labeled 202 may represent the molecular weight markers, the lane labeled 204 may represent the positive control, the lane labeled 206 may represent the negative control, the lane labeled 208 may represent Person A, the lane labeled 210 may represent Person B, the lane labeled 212 may represent Person C, the lane labeled 214 may represent Person D, and the lane labeled 216 may represent Person E. An electronic image of the complete gel, i.e., including all eight lanes thereon, subsequently may be received at block 102 (FIG. 2A), e.g., captured via a CCD camera or the like.

Subsequently, a technician may wish to associate the common lanes and the lane particular to Person C with an electronic medical record correlated with Person C for later viewing and evaluation by a clinician. In this regard, the technician may prompt the system to retrieve the gel loading data from a batch list associated with the gel loading process 110, the batch list being generated, for instance, by the clinical laboratory system, and note that the lanes labeled 202, 204, and 206 are common lanes (as shown at block 112), and that the lane labeled 212 is particular to Person C (as shown at block 114). The technician may also note that the lanes labeled 208, 210, 214, and 216 are neither common nor particular to Person C.

The technician then may parse the complete gel image into two separate image portions, as shown at block 116. Referring to FIG. 3A, the first image portion may be a common image portion which includes all three common lanes 202, 204, and 206, and the second image portion may be particular to Person C and include only the lane labeled 212. Next, the technician (or the system itself) may associate the common and individual image portions (as shown at block 118 of FIG. 2A), and, if desired, may collapse them together.

The system subsequently may retrieve the electronic medical record correlated with Person C (as shown at block 120), associate a gel ID number with each image portion, and separately store the common image portion and the image portion which is particular to Person C with the electronic medical record correlated with Person C. This is shown at block 122. Alternatively, the system may aggregate the common image portion and the image portion which is particular to Person C into a single hybrid image (as shown at block 124), associate the gel ID number with the hybrid image, and store the hybrid image with the electronic medical record correlated with Person C. This is shown at block 126.

Subsequently, a clinician evaluating Person C may wish to view the gel image to determine whether or not Person C is HIV+. Accordingly, the clinician may prompt the system to retrieve the electronic medical record correlated with Person C which includes the separately stored common image portion and the image portion which is particular to Person C. The clinician may then view the image portions, for instance, in side-by-side orientation. In this regard, the system monitor may include a view similar to that shown in FIG. 5. Alternatively, if the image portions were stored as a hybrid image, the system may simply retrieve the hybrid image from the electronic medical record correlated with Person C. The clinician may then note that, as the lane labeled 212 (i.e., the lane particular to Person C) indicates a pattern like that of the lane labeled 204 (i.e., the positive control lane), Person C may be diagnosed as HIV+.

Figure 2B:
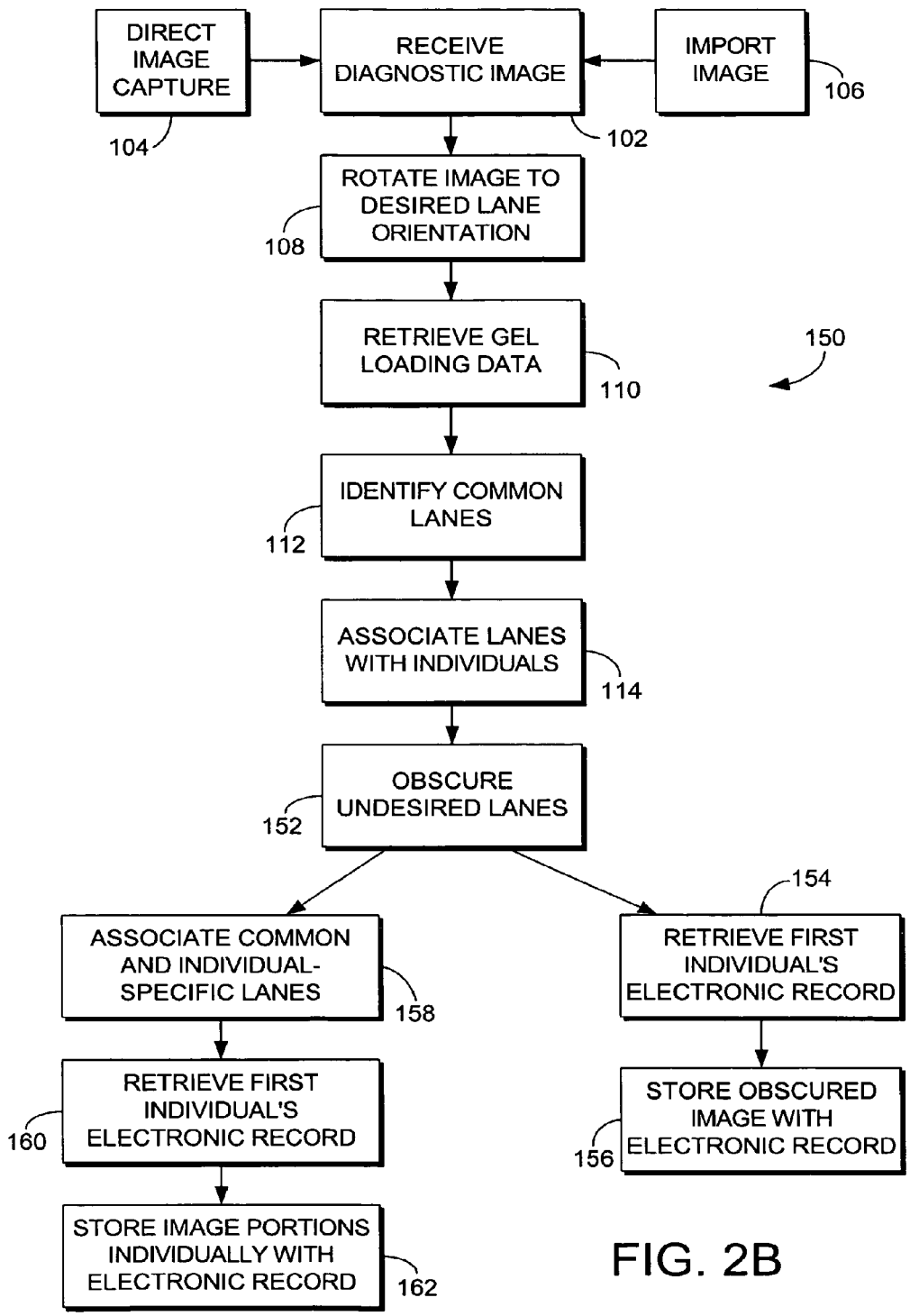
FIG. 2B is a flow chart representative of a computer program for associating at least a portion of an obscured diagnostic image with an electronic record in accordance with an embodiment of the present invention.

Referring now to FIG. 2B, a method 150 for obscuring at least a portion of a diagnostic image and associating the obscured image with the electronic record of an individual whose data is shown thereon is provided. Blocks 102, 104, 106, 108, 110, 112, and 114 of FIG. 2B are the same as the identically numbered blocks of FIG. 2A and, accordingly, are not described further herein.

Figure 6:
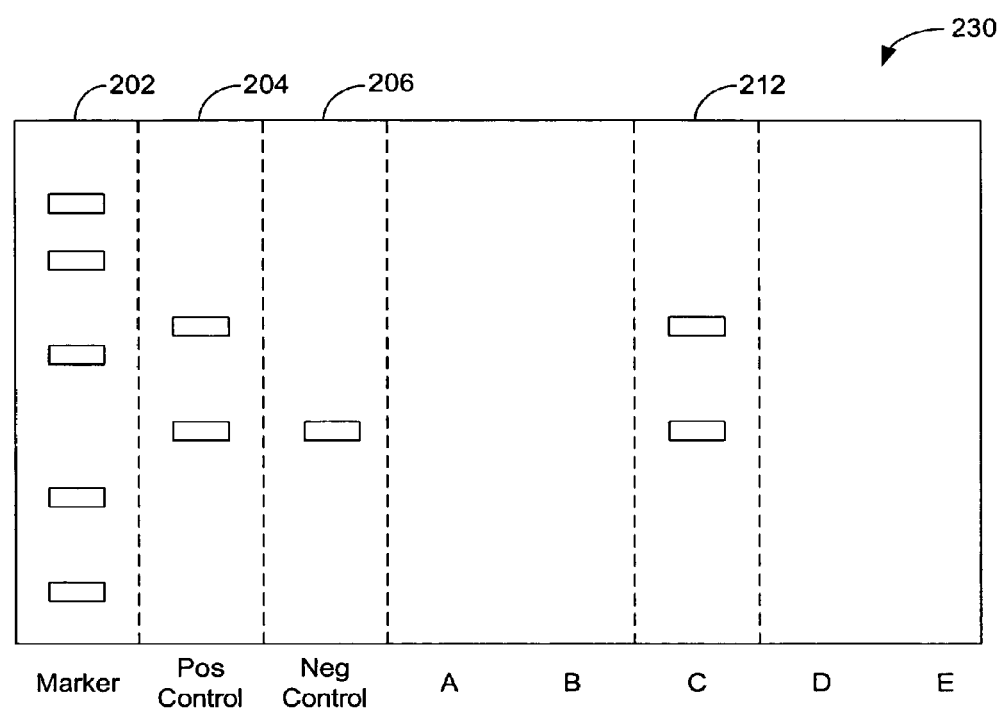
FIG. 6 is a schematic diagram illustrating an exemplary obscured gel image derived from the complete gel image of FIG. 3A wherein four of the eight lanes have been obscured in accordance with an embodiment of the present invention.

In the embodiment of FIG. 2B, after the lanes which are not identified as common lanes are associated with the individual whose data is shown thereon, as indicated at block 114, those lanes for which association is not desired are hidden or obscured from view, preferably permanently obscured. This obscuring, which may be performed manually by a user or automatically by the system upon appropriate user input, is shown at block 152. Lanes for which association is not desired may include all lanes which are not identified as common lanes and all lanes which are identified as being particular to individuals other than the first individual, i.e., the individual for whom association is being performed. For instance, an exemplary obscured diagnostic gel image is shown in FIG. 6 and designated generally as reference numeral 230. The obscured gel image 230 is derived from the complete diagnostic gel image 200 shown in FIG. 3A. Visible in the obscured image 230 (FIG. 6) are only those lanes which are common lanes 202, 204, 206 and the lane labeled 212 which is particular to Person C. Obscured are lanes 208 (specific to Person A), 210 (specific to Person B), 214 (specific to Person D), and 216 (specific to Person E) of FIG. 3A.

Next, as shown at block 154 (FIG. 2B), the system may retrieve an electronic record, e.g., an electronic medical record, particular to a first individual whose data is shown on the image. For example, in the example illustrated in FIG. 6, an electronic record particular to Person C may be retrieved.

Subsequently, as shown at block 156, the system may associate an identifier related to the complete gel image with the obscured image and store the obscured image with the first individual's electronic record. As such, upon retrieval of the first individual's electronic record, the obscured image may be retrieved and viewed. In the example illustrated in FIG. 6, the obscured image 230 may be associated and stored with an electronic record particular to Person C.

Referring back to FIG. 2B, in another embodiment, an obscured common image portion and an obscured image portion particular to a first individual whose data is shown on the image may be created at block 152. Subsequently, the system may associate all obscured common image portions with the image portion or portions which are particular to the first individual. This is shown at block 158. Next, as shown at block 160, the system may retrieve an electronic record, e.g., an electronic medical record, correlated with the first individual, i.e., the individual whose data was associated with the obscured common image portion at block 158. Then, the system may individually store the associated image portions with the first individual's electronic record, as shown at block 162.

In this embodiment, the system may associate an identifier related to the complete gel image, e.g., a gel ID number, with each stored image portion. Thus, upon retrieval of the first individual's electronic record, each image portion may be separately retrieved and viewed, for instance, in side-by-side orientation or overlaid, one upon the other.

Blocks 152, 154, 156, 158, 160, and 162 may be repeated for each individual whose data is shown on the complete diagnostic image, e.g., diagnostic gel image 200 (FIG. 3A). As with the method shown in FIG. 2A, once all relevant data has been associated and stored with the electronic record(s) of the person(s) whose data is shown on the complete diagnostic image, the complete image may be destroyed or stored in a location not correlated with any one person's electronic record. In this way, the privacy of all individuals whose data is shown on the image may be maintained.

It will be understood and appreciated by those of ordinary skill in the art that the blocks of method 150 may take place in an order other than the exemplary sequence illustrated in FIG. 2B.

In operation, by way of example only, suppose an agarose gel is loaded with three control samples and samples particular to each of five persons, Persons A-E, as set forth above with regard to the method of FIG. 2A. Once the gel has been run and an image thereof captured or imported, the system may retrieve the gel loading data from a batch list associated with the gel loading process (as shown at block 110), identify the common lanes (as shown at block 112) and associate the lanes that are particular to a specific person with that person (as shown at block 114). Subsequently, the system, upon appropriate user input, may obscure the undesired lane, i.e., those lanes which are neither common nor associated with the person of interest, in this case, Person C. This is shown at block 152.

If the undesired lanes are obscured to create two separate image portions, one including the common lanes and one including only the lane labeled 212 which is particular to Person C, the system subsequently may associate the common lanes 202, 204, 206 with the lane particular to Person C, the lane labeled 212. This is shown at block 158 of FIG. 2B. If, however, the undesired lanes were obscured to create a single image such as the image shown in FIG. 6, the common lanes 202, 204, 206 and the lane particular to Person C 212 are already associated with one another.

Subsequently, the system may retrieve the electronic medical record correlated with Person C (as shown at block 160), associate a gel ID number with each image portion, and separately store the common image portion and the image portion which is particular to Person C with the electronic medical record correlated with Person C, as shown at block 162. Alternatively, if the undesired lanes were obscured to create a single obscured image, the system may retrieve the electronic medical record correlated with Person C, as shown at block 154, associate the gel ID number with the obscured image, and store the obscured image with the electronic medical record correlated with Person C, as shown at block 156.

Subsequently, a clinician evaluating Person C may wish to view the gel image to determine whether or not Person C is HIV+. Accordingly, the clinician may prompt the system to retrieve the electronic medical record correlated with Person C which includes the separately stored common image portion and the image portion which is particular to Person C, or the single obscured image having both the common data and the data particular to Person C.

Another method (not shown) is provided for associating at least a portion of a diagnostic image with the electronic record of an individual whose data is shown thereon and includes determining the coordinates of a complete diagnostic image that are specific to any common lanes that are present on the image and all lanes that are specific to a particular individual and persistently storing those coordinates with an electronic record correlated with the individual. Subsequently, upon retrieval of the individual's electronic record, the system may retrieve only those portions of the diagnostic image indicated by the stored coordinates and display them on a user interface, e.g., a monitor. This approach does not require the generation and storage of multiple small image files but the coordinates are susceptible to changes in the structure of the original complete diagnostic image, which complete image may be stored independent of the electronic record associated with any particular individual.

While the examples and discussion in this document focus on one dimensional gel electrophoresis, this invention is equally applicable to the management of patient information generated using two-dimensional techniques (for example, in proteomic analysis) and other variations of gel-based analysis.

Additionally, the present invention is equally applicable to the management of patient information generated using other one-dimensional diagnostic techniques. Without limitation, such techniques may include diagnostic spot assays. By way of example only, a diagnostic spot assay may be generated by overlaying a substrate with an antibody for a protein, e.g., an HIV-related protein. Subsequently, sera from a number of individuals may be spotted onto the substrate and a radioactive marker used to determine whether or not any particular individual has antibodies against the detected protein. When the substrate is washed off, dark blotches may appear for those individuals having antibodies against the HIV-related protein while no visible marking may be present for those individuals without antibodies against the protein. An image of the spot assay may subsequently be captured, which image includes test results from all persons whose sera was spotted onto the substrate.

The present invention provides computerized methods and systems for associating at least a portion of a diagnostic image, the diagnostic image including data specific to at least two persons, with an electronic record, for instance, an electronic medical record. Although the invention has been described with reference to the preferred embodiments illustrated in the attached drawing figures, it is noted that substitutions may be made and equivalents employed herein without departing from the scope of the invention recited in the claims. For instance, additional steps may be added and steps may be omitted without departing from the scope of the invention.

The invention claimed is:

1. A method in a computing environment for associating one or more portions of a diagnostic image with at least one electronic medical record, the method comprising:

receiving the diagnostic image in an electronic format, the diagnostic image including data particular to at least two persons, wherein the diagnostic image is an image of a gel result;

when the diagnostic image is determined to be skewed in orientation, rotating the diagnostic image to a proper alignment;

receiving gel loading data associated with the diagnostic image;

based on the gel loading data, identifying common lanes of the diagnostic image;

based on the gel loading data, identifying at least one lane of the diagnostic image particular to a first of the at least two persons and at least one lane of the diagnostic image particular to a second of the at least two persons;

modifying the diagnostic image to create a modified image, wherein modifying the diagnostic image comprises parsing the at least one lane of the diagnostic image particular to the second of the at least two persons from the diagnostic image to create the modified image, the modified image comprising the at least one lane of the diagnostic image particular to the first of the at least two persons; and storing the modified image with an electronic medical record for the first of the at least two persons.

2. The method of claim 1, wherein receiving the diagnostic image comprises at least one of capturing the diagnostic image or importing the diagnostic image.

3. The method of claim 1, wherein the rotating of the diagnostic image is automatically performed by a computing system.

4. The method of claim 1, further comprising parsing all lanes other than the identified common lanes of the diagnostic image to create a common image portion, the common image portion consisting of data common to each of the at least two persons.

5. The method of claim 4, wherein the data common to each of the at least two persons comprises at least one of a molecular weight marker, a positive control, or a negative control.

6. The method of claim 4, further comprising storing the common image portion with the electronic medical record for the first of the at least two persons.

7. The method of claim 4, further comprising:
aggregating the modified image and the common image portion to create a hybrid image; and
storing the hybrid image with the electronic medical record for the first of the at least two persons.

8. The method of claim 7, further comprising storing the hybrid image with the electronic medical record for the first of the at least two persons.

9. The method of claim 1, wherein the modified image comprises data particular to the first of the at least two persons and the common lanes of the diagnostic image.

10. The method of claim 9, wherein the common lanes of the diagnostic image comprises at least one of a molecular weight marker, a positive control, or a negative control.

11. The method of claim 9, wherein the common lanes of the diagnostic image represent data which is common to all persons having data represented on the diagnostic image.

12. A method in a computing environment for associating one or more portions of a diagnostic image with at least one electronic medical record, the method comprising one or more computers implementing the following steps:
receiving the diagnostic image in an electronic format, the diagnostic image including data particular to at least two persons, wherein the diagnostic image is an image of a gel result;
when the diagnostic image is determined to be skewed in orientation, rotating the diagnostic image in proper alignment;
receiving gel loading data associated with the diagnostic image;
based on the gel loading data, identifying common lanes of the diagnostic image;
based on the gel loading data, identifying at least one lane of the diagnostic image particular to a first of the at least two persons and at least one lane of the diagnostic image particular to a second of the at least two persons;
modifying the diagnostic image to create a modified image, wherein modifying the diagnostic image comprises obscuring the at least one lane of the diagnostic image particular to the second of the at least two persons to create the modified image, the modified image comprises the at least one lane of the diagnostic image particular to the first of the at least two persons; and storing the modified image with an electronic medical record for the first of the at least two persons.

13. The method of claim 12, wherein the rotating of the diagnostic image is automatically performed by a computing system.

14. The method of claim 12, further comprising obscuring all lanes other than the identified common lanes of the diagnostic image to create a common image portion, the common image portion consisting of data common to each of the at least two persons.

15. The method of claim 14, wherein the data common to each of the at least two persons comprises at least one of a molecular weight marker, a positive control, or a negative control.

16. The method of claim 14, further comprising storing the common image portion with the electronic medical record for the first of the at least two persons.

17. The method of claim 14, further comprising:
aggregating the modified image and the common image portion to create a hybrid image; and
storing the hybrid image with the electronic medical record for the first of the at least two persons.

18. The method of claim 17, further comprising storing the hybrid image with the electronic medical record for the first of the at least two persons.

19. The method of claim 12, wherein the modified image comprises the at least one lane of the diagnostic image particular to the first of the at least two persons and the common lanes of the diagnostic image.

20. The method of claim 19, wherein the data common to each of the at least two persons comprises at least one of a molecular weight marker, a positive control, and a negative control.

21. The method of claim 19, wherein the common lanes of the diagnostic image represent data which is common to the at least two persons.

22. A non-transitory computer-readable medium having computer-executable instructions embodied thereon, that when executed by a computing system having a processor and memory, cause the computing system to perform a method, the method comprising:
receiving a diagnostic image, of a gel, in an electronic format that is readable by the computing system, the diagnostic image including data particular to at least two persons;
when the diagnostic image is determined to be skewed in orientation, rotating the diagnostic image to a proper alignment;
receiving gel loading data associated with the diagnostic image, wherein the gel loading data indicates which lanes of the diagnostic image are indicative of common data and which lane is particular to an individual person;
based on the gel loading data, identifying common lanes of the diagnostic image, wherein the common lanes include data common to the two or more persons having data represented on the diagnostic image;
based on the gel loading data, identifying at least one lane of the diagnostic image particular to a first of the at least two persons and at least one lane of the diagnostic image particular to a second of the at least two persons;

modifying the diagnostic image to create a modified image, wherein modifying the diagnostic image comprises parsing all data other than the at least one lane of the diagnostic image particular to the first of the at least two persons from the diagnostic image; to create the modified image;

modifying the diagnostic image to create a common image, wherein modifying the diagnostic image comprises parsing all data other than the common lanes of the diagnostic image from the diagnostic image to create the common image;

aggregating the modified image and the common image portion to create a hybrid image; and storing the hybrid image with an electronic medical record for the first of the at least two persons.

* * * * *